United States Patent [19]

Sanderson et al.

[11] Patent Number: 5,180,869
[45] Date of Patent: * Jan. 19, 1993

[54] PROCESS FOR CO-REACTING POLY(ISOBUTYLENE) AND LINEAR OLEFINS TO PREPARE SYNTHETIC LUBRICANT BASE STOCKS HAVING IMPROVED PROPERTIES

[75] Inventors: John R. Sanderson, Leander; Edward T. Marquis, Austin, both of Tex.

[73] Assignee: Texaco Chemical Company, White Plains, N.Y.

[*] Notice: The portion of the term of this patent subsequent to Oct. 1, 2008 has been disclaimed.

[21] Appl. No.: 699,533

[22] Filed: May 14, 1991

[51] Int. Cl.$^5$ ................................................ C07C 2/74
[52] U.S. Cl. ...................................... 585/255; 585/533
[58] Field of Search ................................ 585/255, 533

[56] References Cited

U.S. PATENT DOCUMENTS

| | | | |
|---|---|---|---|
| 2,951,087 | 8/1960 | Hauser et al. | 502/62 |
| 3,412,039 | 11/1968 | Miller | 252/428 |
| 3,432,571 | 3/1969 | Noddings et al. | 260/641 |
| 3,459,815 | 8/1969 | Noddings et al. | 260/641 |
| 3,845,150 | 10/1974 | Tsoung-Yuan Yan et al. | 208/135 |
| 3,849,507 | 11/1974 | Zuech | 260/671 C |
| 4,153,638 | 5/1979 | Bercik et al. | 585/526 |
| 4,299,730 | 11/1981 | Sommer et al. | 252/435 |
| 4,351,980 | 9/1982 | Reusser et al. | 585/820 |
| 4,380,509 | 4/1983 | Sommer et al. | 252/453 |
| 4,456,779 | 6/1984 | Owen et al. | 585/415 |
| 4,480,142 | 10/1984 | Cobb | 585/464 |
| 4,531,014 | 7/1985 | Gregory et al. | 585/415 |
| 4,604,491 | 8/1986 | Dressler et al. | 585/26 |
| 4,620,048 | 10/1986 | Ver Strate et al. | 585/10 |
| 4,788,362 | 11/1988 | Kaneko | 585/10 |
| 4,808,559 | 2/1989 | Sommer et al. | 502/63 |
| 4,827,064 | 5/1989 | Wu | 585/530 |
| 4,879,425 | 11/1989 | Kukes et al. | 585/530 |
| 4,962,262 | 10/1990 | Winter et al. | 585/512 |
| 4,968,853 | 11/1990 | Scharf | 585/10 |
| 5,030,791 | 7/1991 | Sanderson et al. | 585/520 |
| 5,053,569 | 10/1991 | Marquis et al. | 585/533 |

OTHER PUBLICATIONS

Figueras, "Pillared Clays as Catalysts," Catal. Rev.-Sci. Eng., 30(3), pp. 457-499 (1988).
Friedlander, "Organized Polymerization. I. Olefins on a Clay Surface," Journal of Polymer Science: Part C, No. 4, pp. 1291-1301.
Friedlander et al., "Organized Polymerization III. Monomers Intercalated in Montmorillonite," Polymer Letters, vol. 2, pp. 475-479 (1964).
"Intercalated Catalysts and Pillared Clays," from a Process Evaluation/Research Planning Report by Chem Systems, titled "Catalysts: Selected Developments," 84-3, pp. 239-249 (Dec. 1985).
Boland, "Synthetic Lubricant Base Stocks," Process Economics Program Report No. 125A by SRI International, Apr. 1989 and Supplemental A, Sep. 1989.
"Synthetic Lubricants from Internal Olefins," Process Evaluation/Research Planning Report by Chem Systems, 84-Q-1, pp. 17-45.
Adams, "Synthetic Organic Chemistry Using Pillared, Cation-Exchanged and Acid-Treated Montmorillonite Catalysts—A Review", Applied Clay Science, 2 (1987) pp. 309-342.
Adams et al., in "Clays as Selective Catalysts in Organic Synthesis," Journal of Inclusion Phenomena, vol. 5, (1987), pp. 663-674.
Purnell, "Catalysis by Ion-Exchanged Montmorillonites," Catalysis Letters, 5 (1990), pp. 203-210.
Kuliev et al., "Preparation of High-Viscosity Synthetic Lubricants Using an Aluminosilicate Catalyst," Institute of Petrochemical Processes of the Academy of Sciences of the Azerbaidzhan SSR, Azerbaidzhanskoe. Neftiano, Khoziaistvo., 1983, No. 4, pp. 40-43.
Chaudhuri and Sharma, "Some Novel Aspects of the Dimerization of L-Methylstyrene with Acidic Ion-Exchange Resins, Clays, and Other Acidic Materials as Catalysts," Ind. Eng. Res., vol. 28, pp. 1757-1763 (1989).

Primary Examiner—Patrick P. Garvin
Assistant Examiner—E. D. Irzinski
Attorney, Agent, or Firm—Jack H. Park; Kenneth R. Priem; Russell R. Stolle

[57] ABSTRACT

A process is disclosed for preparing synthetic lubricant base stocks having improved properties. Synthetic lubricant base stocks may be prepared in good yield by oligomerizing linear olefins using certain acidic montmorillonite clay catalysts. When a mixture of poly(isobutylene) and long-chain linear olefin, in which up to about 10 wt. % of the mixture is poly(isobutylene), is co-reacted in the presence of these catalysts, a synthetic lubricant base stock having a high viscosity and a high viscosity index is prepared.

20 Claims, No Drawings

PROCESS FOR CO-REACTING POLY(ISOBUTYLENE) AND LINEAR OLEFINS TO PREPARE SYNTHETIC LUBRICANT BASE STOCKS HAVING IMPROVED PROPERTIES

CROSS-REFERENCE TO RELATED APPLICATIONS

This application is related to the following co-pending U.S. patent applications: Ser. No. 07/500,631, filed Mar. 28, 1990, which relates to the preparation of synthetic lubricant base stocks by oligomerizing linear olefins by means of certain acidic montmorillonite clays; Ser. No. 07/516,931, filed Apr. 30, 1990, which relates to the preparation of synthetic lubricant base stocks by oligomerizing certain mixtures of internal and alpha-olefins by means of certain acidic montmorillonite clays; Ser. No. 07/516,870, filed Apr. 30, 1990, which relates to synthetic lubricant base stocks made by oligomerizing linear olefins by means of certain aluminum nitrate-treated acidic montmorillonite clays; Ser. No. 07/522,941, filed May 14, 1990, which relates to the preparation of synthetic lubricant base stocks by co-oligomerizing propylene and long-chain alpha-olefins by means of certain acidic montmorillonite clay catalysts; Ser. No. 07/525,807, filed May 21, 1990, which concerns synthetic lubricant base stocks made by co-oligomerizing 1,3-di-isopropenyl benzene and long-chain alpha-olefins by means of certain acidic montmorillonite clay catalysts; Ser. No. 07/531,172, filed May 31, 1990, which concerns synthetic lubricant base stocks having an improved pour point; Ser. No. 07/534,080, filed Jun. 6, 1990, which concerns synthetic lubricant base stocks having an improved viscosity; Ser. No. 07/536,906, filed Jun. 12, 1990, which concerns synthetic lubricant base stocks made by co-reacting olefins and anisole or like compounds; Ser. No. 07/545,260, filed Jun. 28, 1990, which concerns mixtures of oligomers and certain alkylated aromatics as synthetic lubricant base stocks; Ser. No. 07/551,969, filed Jul. 12, 1990, which concerns a process for oligomerizing olefins using phosphorous-containing acid on montmorillonite clay; Ser. No. 07/577,385, filed Aug. 31, 1990, which concerns synthetic lubricant base stocks prepared from long-chain vinylidene olefins and long-chain alpha and/or internal olefins; Ser. No. 07/580,439, filed Sep. 10, 1990, which concerns synthetic lubricant base stocks by co-reaction of vinylcyclohexene and long-chain olefins; Ser. No. 07/676,492, filed Mar. 28, 1991, which concerns a process for preparing synthetic lubricant base stocks having improved viscosity from vinylcyclohexene and long-chain olefins. The totality of each of these previously filed applications is incorporated herein by reference.

BACKGROUND OF THE INVENTION

1. Field of the Invention

The invention relates to the preparation of synthetic lubricant base stocks, and more particularly to synthetic lubricant base stocks having improved properties, made by co-reacting poly(isobutylene) and long-chain linear olefins by means of certain acidic montmorillonite clay catalysts.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt or higher are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium or high viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $m^2/g$ or greater. In addition to being excellent catalysts, these clays are non-hazardous and non-polluting. With respect to the present invention, Applicants have found, surprisingly, that a high yield of synthetic lubricant base stocks with a much higher viscosity and a much higher viscosity index may be obtained where the base stocks are prepared by co-reacting a mixture of up to about 10 wt. % poly(isobutylene) and more than about 90 wt. % long-chain linear olefin in the presence of these clay catalysts.

SUMMARY OF THE INVENTION

The invention relates to a process for the preparation of high viscosity synthetic lubricant base stocks, comprising contacting (1) a mixture of poly(isobutylene) and a linear olefin having from 10 to 24 carbon atoms, wherein up to about 10 wt. % of the mixture is poly(isobutylene), with (2) a catalytically effective amount of an acidic calcium montmorillonite clay having a moisture content ranging up to about 20 wt. %, a residual acidity in the range of about 3 to about 30 mg KOH/g, and a surface area of about 300 $m^2/g$ or greater. The invention also relates to a process for the preparation of high viscosity synthetic lubricant base stocks, comprising contacting (1) a mixture of poly(isobutylene) and a linear olefin having from 12 to 18 carbon atoms, wherein from about 2 to about 5 wt. % of the mixture is poly(isobutylene), with (2) a catalytically effective amount of an acidic calcium montmorillonite clay having a moisture content ranging up to about 20 wt. %, a residual acidity in the range of about 3 to about 30 mg KOH/g, and a surface area of about 300 $m^2/g$ or greater, to obtain a synthetic lubricant base stock having a viscosity at 210° F. greater than about 5 cSt.

DESCRIPTION OF THE PREFERRED EMBODIMENTS

Applicants discovered that synthetic lubricant base stocks may be prepared in high yield without significant by-products by oligomerizing long-chain olefins using certain acidic montmorillonite clay catalysts. Applicants have further discovered that the viscosity and viscosity index of these synthetic lubricant base stocks are substantially raised when the olefin feed comprises a mixture of linear olefin and up to about 10 wt. % poly(isobutylene), preferably from about 0.05 to about 10 wt. % poly(isobutylene). It is especially preferred that the mixture of linear olefin and poly(isobutylene) contains from about 2 to about 5 wt. % poly(isobutylene). The resulting higher viscosity index indicates that the synthetic lubricant will be less susceptible to a change in viscosity when subjected to a change in temperature. Applicants' method, by directly incorporating poly(isobutylene) into the base stocks via co-reaction with the linear olefin feed, avoids the need for a second step of dissolving viscosity enhancing additives and viscosity index improvers into the base stock after the oligomerization is completed. Applicants are able to obtain synthetic lubricant base stocks having a viscosity at 210° F. greater than about 50 cSt, and in some cases greater than about 200 cSt. These same base stocks also have a viscosity index greater than about 200.

Olefin monomer feed stocks useful in the present invention include compounds comprising (1) alpha-olefins having the formula $R''CH=CH_2$, where R" is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. A preferred range for the total number of carbon atoms in any one olefin molecule is 14 to 18, inclusive. An especially preferred range is 14 to 16, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins useful in the present invention may be obtained by processes well-known to those skilled in the art and are commercially available.

The poly(isobutylene) [also referred to in the literature as polybutylene, polybutene, or polyisobutene] to be co-reacted in this invention may be obtained by processes well-known to those skilled in the art (see, for example, Noller, *Chemistry of Organic Compounds*, 3rd. Ed., page 103 (1965), and is commercially available. Preferably, the poly(isobutylene) has an average molecular weight range of from about 50,000 to about 2,000,000 or greater. It is especially preferred that the poly(isobutylene) have an average molecular weight range of from about 100,000 to about 600,000.

The oligomerization of the linear olefin may be represented by the following general equation:

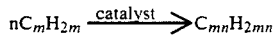
$$nC_mH_{2m} \xrightarrow{catalyst} C_{mn}H_{2mn}$$

where n represents moles of monomer and m represents the number of carbon atoms in the monomer. Thus, the oligomerization of 1-decene may be represented as follows:

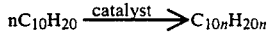
$$nC_{10}H_{20} \xrightarrow{catalyst} C_{10n}H_{20n}$$

The reactions occur sequentially. Initially, olefin monomer reacts with olefin monomer to form dimers. Some of the dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond. Most of the poly(isobutylene) present in the reaction mixture does not react with the linear olefin, but remains dispersed in the resulting base stock as poly(isobutylene). However, because the poly(isobutylene) does contain some unsaturation, in the form of a terminal vinyl group, some of the poly(isobutylene) will co-oligomerize with the linear olefin feed.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

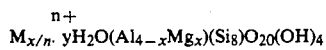
$$M_{x/n} \cdot yH_2O(Al_{4-x}Mg_x)(Si_8)O_{20}(OH)_4$$

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 m²/g or greater. Illustrative examples include Filtrol grade 24, having a moisture content of 12 wt. %, a residual acidity of 8.5 mg KOH/g, and a surface area of 425 m²/g; Filtrol grade 124, having a moisture content of 2 wt. %, a residual acidity of 7.0 mg KOH/g, and a surface area of 400 m²/g; Filtrol grade 13, having a moisture content of 16 wt. %, a residual acidity of 15 mg KOH/g, and a surface area of 300 m²/g; Filtrol grade 113, having a moisture content of 4 wt. %, a residual acidity of 10 mg KOH/g, and a surface area of 300 m²/g; and Filtrol grade 224, having virtually no moisture, and having a residual acidity of 3.0 mg KOH/g, and a surface area of 350 m²/g.

Preferably, the catalyst is activated by heat treatment before running the reaction. Applicants found, surprisingly, that heat treatment of the catalyst prior to running the oligomerization reaction causes the catalyst to be more active and produce a higher olefin conversion. Additionally, clays heat-treated in this manner are more stable, remaining active during the oligomerization reaction for a longer period of time. The clays may be heat-treated at temperatures in the range of about 50° to 400° C., with or without the use of a vacuum. A more preferred temperature range is 50° to 300° C. Optionally, an inert gas may be used during heat treatment as well. Preferably, the clay should be heat-treated under conditions and for a length of time which will reduce the water content of the clay to approximately 1 wt. % or less.

The oligomerization reaction may be carried out in either a stirred slurry reactor or in a fixed bed continuous flow reactor. The catalyst concentration should be sufficient to provide the desired catalytic effect. The temperatures at which the oligomerization may be performed are between about 50° and 300° C., with the preferred range being about 150° to 180° C., for optimum conversion. At temperatures of about 200° C. or greater, the amount of unsaturation remaining in the products of the oligomerization reaction may decrease, thus reducing the degree of hydrogenation necessary to remove unsaturation from the base stocks. However, at temperatures above 200° C., the olefin conversion may decrease and the dimer to trimer ratio to increase. Applicants have found that the addition of a hydrocarbon containing a tertiary hydrogen, such as methylcyclohexane, may further reduce the amount of unsaturation present in the base stocks. One skilled in the art may choose the reaction conditions most suited to the results desired for a particular application. The reaction may be run at pressures of from 0 to 1000 psig.

Following the oligomerization reaction, the unsaturated oligomers and poly(isobutylene) may be hydrogenated to improve their thermal stability and to guard against oxidative degradation during their use as lubricants. The hydrogenation reaction for 1-decene oligomers may be represented as follows:

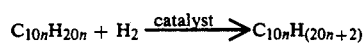
$$C_{10n}H_{20n} + H_2 \xrightarrow{catalyst} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

While it is known to include a distillation step after the hydrogenation procedure to obtain products of various 100° C. viscosities, it is preferred in the method of the present invention that no further distillation (beyond monomer flashing) be conducted. In other words, the monomer-stripped, hydrogenated bottoms are the desired synthetic lubricant components. Thus, the method of this invention does not require the costly, customary distillation step, yet, surprisingly, produces a synthetic lubricant component that has excellent propreaction, the mixture was cooled to below 100° C., and filtered with suction. The mixture was analyzed by high pressure liquid chromatography. Percent conversions obtained and dimer/trimer ratios are shown in the attached table.

Hydrogenation

The reactor effluent was then charged to a stainless steel reactor along with 5 wt. % nickel catalyst. The reactor was flushed three times with hydrogen and then pressured to 1000 psig with hydrogen. The mixture was heated to 200° C., pressured to 2000 psig with hydrogen, and stirred at this temperature for 4 hours. The mixture was then repressured with hydrogen to 2000 psig, as needed. The mixture was then cooled to below 100° C., and filtered with suction. The filtrate was vacuum distilled (<1 mm Hg) to a head temperature of 150° C. Properties of the bottoms product are recorded in the table below.

| | | | | Co-Reaction of Linear Olefins With Various Polymers | | | | | | | |
|---|---|---|---|---|---|---|---|---|---|---|---|
| Ex. No. | Olefin | (g) of olefin | Polymer | (g) of pol. | Remarks (about polymer) | Conv. (%) | D/T+ | Vis @ 210° F. | VI | Noack (%) | CCSM (cp) | Pour Point (°F.) |
| 1 | 14a | 390 | PMP | 10 | MI = 70 | 81.9 | 1.28 | 5.38 | 135 | 14.1 | 729 | −20 |
| 2 | 14a | 390 | PBD | 10 | MW = 4500 | 49.5 | 3.90 | 6.01 | 153 | 16.0 | 805 | −15 |
| 3 | 14a | 390 | PBI | 10 | MI = 20* | 83.7 | 1.17 | n.d. | n.d. | n.d. | n.d. | n.d. |
| 4 | 14a | 390 | PIB | 10 | MW = 380000 | 82.7 | 1.26 | 53.40 | 226 | 13.3 | n.d. | −15 |
| 5 | 14a | 390 | PIP | 10 | TM = 36° C. | 70.9 | 1.74 | 5.92 | 134 | 15.3 | n.d. | −15 |
| 6 | 16a | 390 | PIB | 10 | MW = 380000 | 76.5 | 1.41 | 65.00 | 228 | 6.2 | n.d. | −20 |
| 7 | 16a | 390 | PMP | 10 | MI = 70 | 79.1 | 1.93 | 6.85 | n.d. | 7.2 | n.d. | 5 |
| 8 | 1416a | 390 | PIB | 10 | MW = 380000 | 74.1 | 2.00 | 67.70 | 235 | 11.2 | n.d. | −15 |
| 9 | 1416a | 390 | PMP | 10 | MI = 70 | 78.3 | 1.75 | 5.50 | 143 | 13.1 | 710 | −20 |
| 10 | 1518i | 390 | PIB | 10 | MW = 380000 | 53.9 | 3.58 | 123.00 | 252 | 10.4 | n.d. | 0 |
| 11 | 1518i | 390 | PMP | 10 | MI = 70 | 65.7 | 2.37 | 6.17 | 137 | 9.7 | 1051 | −20 |
| 12 | 14a | 390 | PIB | 10 | MW = 1290 | 79.9 | 1.23 | 5.80 | 142 | 15.7 | 814 | −25 |
| 13 | 14a | 390 | PIB | 10 | MW = 2060 | 81.0 | 1.11 | 6.43 | 148 | 14.7 | 939 | −20 |
| 14 | 14a | 390 | PIB | 10 | MW = 2300 | 79.8 | 1.45 | 6.31 | 145 | 13.5 | 951 | −30 |

*Polymer solid at ambient temperature, on reduction.
Conv. = conversion; D = dimer; T+ = trimer + tetramer + higher oligomers; Vis = viscosity; VI = viscosity index; CCSM = cold crank simulation; cp = centipoise; a = alpha, e.g., 14a = $C_{14}$ alpha olefin; i = internal, e.g., 1518i = $C_{15}$ internal, $C_{18}$ internal olefin mixture; n.d. = not determined; PMP = Poly(4-methyl-1-pentene); PBO = Poly(butadiene); PBI = Poly(1-butene), isotactic; PIB = Poly(isobutylene); PIP = Poly(isoprene); MI = melt index; MW = molecular weight; and TM = melting temperature of polymer.

erties and that performs in a superior fashion. However, in some contexts, one skilled in the art may find subsequent distillation useful in the practice of this invention.

The monomer stripping step should be conducted under mild conditions. Distillation at temperatures exceeding 250° C. may cause the oligomers to break down in some fashion and come off as volatiles. Preferably, therefore, the reboler or pot temperature should be kept at or under about 225° C. when stripping out the monomer.

The invention will be further illustrated by the following examples, which are given by way of illustration and not as limitations on the scope of this invention. The entire text of every patent, application or other reference mentioned herein is incorporated herein by reference.

EXAMPLES

The examples summarized in the table below demonstrate the use of the present invention in batch reaction systems:

Procedure

Linear olefin, polymer, and 10 wt. % Harshaw/Filtrol Clay-13 catalyst were charged to a flask equipped with a stirrer, heating mantle, water cooled condenser, and nitrogen purge. The mixture was heated to a temperature of 160° C. for 5.0 hours. At the end of the

We claim:

1. A process for the preparation of high viscosity synthetic lubricant base stocks, comprising contacting under effective oligomerization conditions
   (1) a mixture of poly(isobutylene) and a linear olefin having from 10 to 24 carbon atoms, wherein up to about 10 wt. % of the mixture is poly(isobutylene), with
   (2) a catalytically effective amount of an acidic calcium montmorillonite clay having a moisture content ranging up to about 20 wt. %, a residual acidity in the range of about 3 to about 30 mg KOH/g, and a surface area of about 300 m²/g or greater.

2. The process of claim 1, wherein the linear olefin contains from 12 to 18 carbon atoms.

3. The process of claim 1, wherein about 2 to about 5 wt. % of the mixture of poly(isobutylene) and linear olefin is poly(isobutylene).

4. The process of claim 1, wherein the moisture content of the acidic calcium montmorillonite clay is about 12 wt. %, the residual acidity is about 8.5 mg KOH/g, and the surface area is about 425 m²/g.

5. The process of claim 1, wherein the moisture content of the acidic calcium montmorillonite clay is about 2 wt. %, the residual acidity is about 7.0 mg KOH/g, and the surface area is about 400 m²/g.

6. The process of claim 1, wherein the moisture content of the acidic calcium montmorillonite clay is about 16 wt. %, the residual acidity is about 15 mg KOH/g, and the surface area is about 300 m$^2$/g.

7. The process of claim 1, wherein the moisture content of the acidic calcium montmorillonite clay is about 4 wt. %, the residual acidity is about 10 mg KOH/g, and the surface area is about 300 m$^2$/g.

8. The process of claim 1, wherein the moisture content of the acidic calcium montmorillonite clay is essentially nil, the residual acidity is about 3.0 mg KOH/g, and the surface area is about 350 m$^2$/g.

9. The process of claim 1, wherein the poly(isobutylene) has an average molecular weight of from about 100,000 to about 600,000.

10. A process for the preparation of high viscosity synthetic lubricant base stocks, comprising contacting under effective oligomerization conditions
   (1) a mixture of poly(isobutylene) and a linear olefin having from 12 to 18 carbon atoms, wherein up to about 10 wt. % of the mixture is poly(isobutylene), with
   (2) a catalytically effective amount of an acidic calcium montmorillonite clay having a moisture content ranging up to about 20 wt. %, a residual acidity in the range of about 3 to about 30 mg KOH/g, and a surface area of about 300 m$^2$/g or greater.

11. The process of claim 10, wherein about 2 to about 5 wt. % of the mixture of poly(isobutylene) and linear olefin is poly(isobutylene).

12. The process of claim 10, wherein the moisture content of the acidic calcium montmorillonite clay is about 12 wt. %, the residual acidity is about 8.5 mg KOH/g, and the surface area is about 425 m$^2$/g.

13. The process of claim 10, wherein the moisture content of the acidic calcium montmorillonite clay is about 2 wt. %, the residual acidity is about 7.0 mg KOH/g, and the surface area is about 400 m$^2$/g.

14. The process of claim 10, wherein the moisture content of the acidic calcium montmorillonite clay is about 16 wt. %, the residual acidity is about 15 mg KOH/g, and the surface area is about 300 m$^2$/g.

15. The process of claim 10, wherein the moisture content of the acidic calcium montmorillonite clay is about 4 wt. %, the residual acidity is about 10 mg KOH/g, and the surface area is about 300 m$^2$/g.

16. The process of claim 10, wherein the moisture content of the acidic calcium montmorillonite clay is essentially nil, the residual acidity is about 3.0 mg KOH/g, and the surface area is about 350 m$^2$/g.

17. The process of claim 10, wherein the olefin contains from 13 to 16 carbon atoms.

18. The process of claim 10, wherein the poly(isobutylene) has an average molecular weight of from about 100,000 to about 600,000.

19. A process for the preparation of high viscosity synthetic lubricant base stocks, comprising contacting under effective oligomerization conditions
   (1) a mixture of poly(isobutylene) and a linear olefin having from 12 to 18 carbon atoms, wherein from about 2 to about 5 wt. % of the mixture is poly(isobutylene), with
   (2) a catalytically effective amount of an acidic calcium montmorillonite clay having a moisture content ranging up to about 20 wt. %, a residual acidity in the range of about 3 to about 30 mg KOH/g, and a surface area of about 300 m$^2$/g or greater, to obtain a synthetic lubricant base stock having a viscosity at 210° F. greater than about 50 cSt.

20. The process of claim 19, in which the synthetic lubricant base stock has a viscosity index greater than about 200.

* * * * *